(12) United States Patent
Catt et al.

(10) Patent No.: US 6,927,064 B1
(45) Date of Patent: Aug. 9, 2005

(54) FERTILITY COMPUTING METHOD

(75) Inventors: Michael Catt, Wellinborough (GB);
Carole R. Cunningham, Abbey (GB);
Paul H. C. Mundill, Rushden (GB);
Michael E Prior, Rushden (GB);
Stewart Wilson, Irthlingborough (GB);
Zhi G. Zhang, Putnoe (GB)

(73) Assignee: Inverness Medical Switzerland GmbH, Zug (CH)

(*) Notice: Subject to any disclaimer, the term of this patent is extended or adjusted under 35 U.S.C. 154(b) by 835 days.

(21) Appl. No.: 09/655,355

(22) Filed: Sep. 5, 2000

Related U.S. Application Data

(63) Continuation of application No. 08/924,810, filed on Sep. 5, 1997, now abandoned, which is a continuation-in-part of application No. 08/532,457, filed on Sep. 22, 1995, now Pat. No. 6,451,619, and a continuation-in-part of application No. 08/338,141, filed on Nov. 9, 1994, which is a continuation-in-part of application No. 08/266,776, filed on Jun. 29, 1994, now abandoned.

(30) Foreign Application Priority Data

| Sep. 23, 1994 | (GB) | 9419264 |
| Sep. 26, 1994 | (GB) | 9419382 |
| Jan. 31, 1995 | (GB) | 9501863 |

(51) Int. Cl.[7] .................................................. A61B 10/00
(52) U.S. Cl. ........................................ 436/65; 600/551
(58) Field of Search ............................. 436/65; 600/551

(56) References Cited

U.S. PATENT DOCUMENTS

| 3,986,494 A | * | 10/1976 | Preti et al. .................... 600/551 |
| 4,010,738 A | * | 3/1977 | Preti et al. .................... 600/551 |
| 4,036,212 A | * | 7/1977 | Karuhn ......................... 600/551 |
| 4,119,089 A | * | 10/1978 | Preti et al. ..................... 436/65 |
| 4,151,833 A | * | 5/1979 | Polishuk ....................... 600/551 |
| 4,291,028 A | * | 9/1981 | Vorys .......................... 514/178 |
| 4,292,315 A | * | 9/1981 | Vorys .......................... 514/178 |
| 4,465,077 A | | 8/1984 | Schneider |
| 4,693,969 A | * | 9/1987 | Saxena et al. .............. 435/7.94 |
| 4,752,880 A | | 6/1988 | Aeschlimann |
| 4,753,247 A | * | 6/1988 | Kirsner ........................ 600/547 |
| 4,771,791 A | | 9/1988 | Kubouchi |
| 5,118,630 A | * | 6/1992 | Glaze ........................... 436/65 |
| 5,467,778 A | * | 11/1995 | Catt et al. .................... 600/551 |
| 5,508,261 A | * | 4/1996 | Moyle et al. ................... 514/8 |
| 5,657,762 A | * | 8/1997 | Coley et al. ................. 600/549 |
| 5,837,197 A | * | 11/1998 | Porrazzo et al. ............... 422/61 |
| 6,146,333 A | * | 11/2000 | McNeirney et al. ......... 600/551 |
| 6,234,974 B1 | * | 5/2001 | Catt et al. .................... 600/551 |
| 6,451,619 B1 | * | 9/2002 | Catt et al. .................... 436/514 |
| 6,454,726 B1 | * | 9/2002 | Catt et al. .................... 600/551 |

FOREIGN PATENT DOCUMENTS

| EP | 383619 A1 | 8/1990 |
| EP | 653625 A1 | 5/1995 |
| WO | WO 94/02850 | 2/1994 |

* cited by examiner

*Primary Examiner*—Jeffrey Snay
(74) *Attorney, Agent, or Firm*—Oppedahl & Larson, LLP

(57) ABSTRACT

A fertility determining system employing hormone level measuring apparatus on selected days in a menstrual cycle to determine the levels of analytes, i.e., estrone-3-glucuronide ("E3G") and luteinizing hormone ("LH"), in early morning urine. The fertility/infertility signalling algorithm relies upon data characterizing the user earlier in that menstrual cycle, and also upon her analyte pattern in past recent cycles. At a point in a menstrual cycle which is user-dependent, the early morning E3G urine level is compared against the lower E3G level earlier in the cycle. The beginning of the fertile period is signalled when a sufficient E3G increase occurs. The end of the fertile period (and, correspondingly, the reestablishment of a period requiring no contraception) is signalled a period after the LH surge. In the absence of an LH surge in any subject, the end of the fertile phase is signalled a period of time following the peak of the E3G urinary metabolite of estradiol.

4 Claims, 6 Drawing Sheets

FERTILITY COMPUTING METHOD

This application is a continuation of Ser. No. 08/924,810, filed on Sep. 5, 1997, abandoned, which is a continuation-in-part of patent application Ser. No. 08/532,457, now U.S. Pat. No. 6,451,619, filed Sep. 22, 1995 entitled "Monitoring Methods And Devices For Use Therein" which, in turn is a continuation-in-part of application Ser. No. 08/266,776 filed Jun. 29, 1994, now abandoned, and a continuation-in-part of Ser. No. 08/338,141 filed Nov. 9, 1994.

FIELD OF THE INVENTION

This invention relates to computing systems and methodology for medical application and, more specifically, to a system for signalling a fertile period for conception, or an nonfertile period requiring no contraception, based upon hormone and metabolite levels measured in early morning urine.

The invention is particularly, although not solely, concerned with simple practical procedures that can readily be applied by unskilled persons, e.g., in the home, to provide reliable information concerning fertility status as an aid to conception or to contraception as the user wishes. An important objective of the invention is to provide such information while avoiding the necessity for tests to be conducted on a frequent (e.g., daily) basis throughout every ovulation cycle. The necessity for regular, e.g., daily, testing throughout the cycle has characterized many ovulation cycle monitoring systems previously proposed.

BACKGROUND TO THE INVENTION

To provide reliable information concerning fertility status, the user must be given adequate warning of the onset of the fertile phase in the cycle. A wide variety of techniques have been proposed in the art, some relying on the monitoring of one or more parameters which alter as the event of ovulation approaches. Typical parameters which have been invoked are the concentration of a body fluid analyte, such as estradiol and metabolites thereof, for example, estrone-3-glucuronide (E3G). Other parameters that have been used are basal body temperature (which can only provide predictive information of use in subsequent cycles) and various physiological changes such as the characteristics of vaginal mucus.

Many excellent academic studies have been carried out using such parameters. Such studies have established how these parameters can be correlated with the fertility status of an average member of a large population sample. An example is Collins et al. (1981), *Proc. Xth International Congress on Fertility and Sterility*, Publ. MTP Ltd., p. 19–33. An underlying objective in many such studies is to promote conception in individuals previously regarded as being nonfertile.

However, when attempting to develop a practical monitoring system suitable for use by individuals, it is found that many individual subjects do not conform to the average in terms of cycle length and/or the duration and timing of the fertile phase. The extent of variation from one individual to another, and indeed, from one cycle to another in the same individual, renders average population data too unreliable for consistent practical use.

Understandably, because the severe consequence of imperfect advice concerning fertility status may be an unwanted pregnancy, the tendency has been to exercise extreme caution and to require testing of the relevant parameter or parameters throughout the cycle, and particularly right from the onset of the cycle (onset of menses). From the individual user's point of view, it would be advantageous if the necessity for such constant testing could be avoided and, instead, for the testing to be performed over a comparatively brief portion of each cycle. Not merely may this benefit the user in terms of convenience, but the cost of the method may also be reduced if the method utilizes disposable testing devices and only a few such disposable testing devices are required each month.

An example of a system for detecting the onset of ovulation, using water-swellable polymer pellets to "measure" the water content of vaginal mucus, which, apparently increases at the time of ovulation, is described in U.S. Pat. No. 4,151,833 (Polishuk). It is stated that the peak variation in the size of the pellets, as a result of the absorption of water from cervical mucus, is closely related to the LH surge and the variation in basal body temperature. From the experimental data provided in U.S. Pat. No. 4,151,833 (FIG. 8), it appears that the pellet diameter is indeed very closely related to the timing of the LH surge, and in consequence the system proposed cannot in practice provide a reliable warning of the onset of ovulation earlier than that obtainable from a knowledge of the LH concentration.

In EP-A-385621 (Coley et al./Unilever) the defects of ovulation cycle monitoring systems which rely primarily on the change in BBT to estimate the time of ovulation are described, and we propose therein a system which uses regular BBT measurement in combination with a knowledge of other parameters, particularly the measurement of certain urinary hormone levels. A particular proposal is that BBT is measured daily throughout each cycle and is used to estimate the timing of fertility status changes in a forthcoming cycle. During the course of this forthcoming (predicted) cycle, urinary hormone levels are checked at certain times to confirm that the progress of the cycle, as predicted from the previous BBT knowledge, is consistent. Particular hormones selected are E3G, P3G and LH. It is suggested that the level of urinary E3G is measured on at least one day during the interval from day 5 to 7 of the predicted cycle, and again on at least one day during the interval from day 10 to day 15 of the predicted cycle. According to the example in EP 385621, it is sufficient for the hormone level to be either "high" or "low" relative to a threshold value. The emphasis throughout EP 385621 is that occasional hormone level measurements are used to supplement a monitoring system which relies on BBT measurement. There is no suggestion that hormone measurements alone could provide the basis for a reliable fertility monitoring system personalized for an individual subject.

OBJECTIVES OF THE INVENTION

An object of the present invention is to provide a system for determining and presenting the fertility state of an individual subject; which determines the onset and end of the fertile phase; which is personalized to each individual subject; and which operates solely on body fluid analyte measurements.

A further object of this invention is to avoid continued reliance upon data averages obtained from population studies, with its inherent risk that in an individual subject can vary considerably from the population norm.

GENERAL DESCRIPTION OF THE INVENTION

The above and other objects of the present invention are realized in a fertility determining system which employs hormone level measuring apparatus on selected days in a menstrual cycle to determine the levels of analytes, i.e., estrone-3-glucuronide ("E3G" herein) and luteinizing hormone ("LH") in early morning urine. The fertile/nonfertile signalling algorithm relies upon data characterizing the subject earlier in the menstrual cycle, and also upon the woman's hormone pattern in past recent cycles.

Estradiol has several roles in a menstrual cycle. An increase in estradiol is associated with a change in cervical mucus from a more impregnable, biologically inhospitable form to a condition supportive of sperm mobility and survivability. E3G is a major urinary metabolite which correlates well with estradiol levels. In accordance with one aspect of the present invention, at a point in a menstrual cycle which is user-dependent, the early morning E3G urine level is compared against the lower E3G level earlier in the cycle. The beginning of the fertile period is signalled when a sufficient E3G increase occurs.

Impending ovulation is determined by a marked rise in luteinizing hormone (LH). Ovulation occurs within a very few days (e.g., 24–56 hours) of an LH surge—and sperm penetration through the cervical mucus drops rapidly after the LH peak. The end of the fertile period (and, correspondingly, the reestablishment of a period requiring no contraception) is signalled a period of time after the LH surge. In the absence of an LH surge in any subject, the end of the fertile phase is signalled a period of time following the peak of the E3G urinary metabolite of estradiol.

It is thus a feature of the present invention to provide improved fertility/nonfertility determining and signalling apparatus and methodology.

More specifically, it is a feature of the present invention that improved fertility/nonfertility signalling apparatus and methodology invoke a relating small number of tests during the menstrual cycle, using measurement timing and E3G metabolite and LH hormone urinary values specific to each subject to determine and present the inception and end of the fertile period.

DESCRIPTION OF THE DRAWINGS

The above and other features of the present invention will be more fully apparent for a specific illustrative embodiment thereof, described hereinbelow in conjunction with the accompanying drawings, in which:

Referring now to FIG. 1, there is shown electronic data computing apparatus which receives inputs from an analyte measuring module 38. The composite FIG. 1 apparatus acts in accordance with a program and data contained in a memory 18 to selectively illuminate one of a "fertile" signalling light emitting diode 86 or a "nonfertile" signalling light emitting diode 88 (but not both simultaneously). Depending upon which of the LEDs 86 or 88 is activated, the user is presented with a time period during a menstrual cycle when she is fertile to a significant probability and, correspondingly, a period when she is not.

Figure 1:
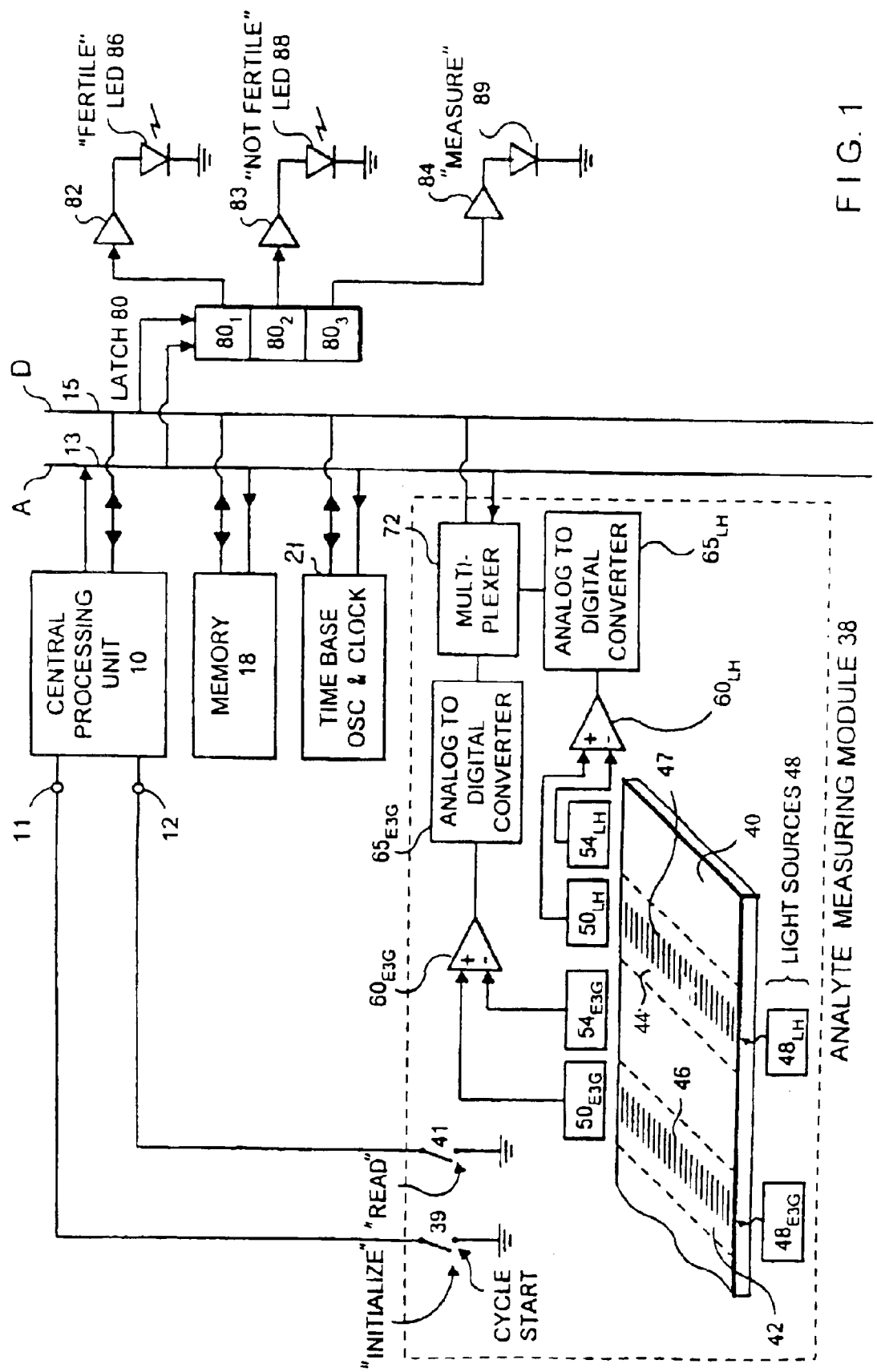
FIG. 1 is a schematic diagram illustrating fertility/nonfertility computing and displaying apparatus in accordance with the principles of the present invention.

The illustrative digital computing apparatus of FIG. 1 includes an address bus 13 and a data bus 15 each connected to a central processing unit 10. Central processing unit 10, per se well known, includes an instruction location counter, read and write (RAM) memory, an accumulator, arithmetic unit and other registers and sub-units as are typical for CPUs. The CPU also has two interrupt ports 11 and 12. Interrupt port 11 is connected to a menstrual cycle ("initialize") start switch 39 in the analyte measuring module 38 which is depressed by a user the first morning after menses (start of flow) to begin a post menstruation cycle. Interrupt port 12 is connected to a read switch 41 which communicates to the CPU that an LH and E3G reading has been taken. The switches may as well be treated as peripherals connected to CPU 10 via the buses 13 and 15.

The memory 18 is connected to the address and data buses 13 and 15, and includes a stored program which operates the composite FIG. 1 system. The memory 18 also stores and furnishes operand and control variable values as more fully discussed below. A time base oscillator and clock 21 is connected to the address and data buses 13 and 15. The time base clock 21 computes and presents to the CPU 10 via the data bus 15 the current day within the menstrual cycle when accessed.

A latch 80 is loaded with three digital bits by the CPU 10 via the address and data buses 13 and 15. The latch 80 includes three storage cells $80_1$, $80_2$ and $80_3$ which respectively drive the LEDs 86, 88 and 89 via amplifiers 82, 83 and 84. At all times, one of the latch cells $80_1$ or $80_2$ includes a binary "1", the other of these two cells including a stored binary "0" such that only one of the LEDs 86 and 88 is illuminated at any time to signal either a fertile or nonfertile condition for the subject. Obviously a latch 80 with only one of the two stages $80_1$ or $80_2$ would suffice to drive both amplifiers 82 and 83, with one of the amplifiers 82 and 83 being inverted such that the LEDs 86 and 88 would always be of opposite states. The third latch stage $80_3$ is set to "1" on the mornings when the FIG. 1 apparatus signals that the user should make urine analyte measurements.

At times and for purposes identified above, but more fully set forth below, it is the purpose of the analyte measuring module 38 to provide to the CPU 10 and memory 18 via the data and address buses 13 and 15 digital measurements of the E3G metabolite and LH hormone levels. Particular illustrative implementations for analyte measurement apparatus are set forth in the above identified co-pending application Ser. No. 532,457, the disclosure of which is incorporated herein by reference in its entirety.

In very brief terms, at times during the menstrual cycle discussed herein, a test strip 40 is exposed to early morning female urine. Early morning urine is preferred, yielding more uniform and reproducible analyte measurements than would otherwise obtain for varying times during an active day. The strip 40 includes a test zone 42 for E3G measurement, and a test zone 44 for LH hormone measurements. Special tagged reagents, e.g., monoclonal antibodies with color tags will adhere to the E3G metabolite in the zone 42, causing a coloration (light blocking) stripe 46 which varies in extent with the level of E3G in the urine. Similarly, a monoclonal antibody specific to the LH hormone will cause a stripe 47 to be formed in the LH measuring zone 44. Again, the stripe 47 (and its light occluding properties) will depend on the amount of LH hormone in the urine sample.

Light sources $48_{E3G}$ and $48_{LH}$ are deposed on one side of the test strip 40, and companion pairs of photodetectors 50 and 54 are deposed on the opposite side of the test strip. Photodetectors $50_{E3G}$ and $50_{LH}$ are employed to measure the background transmissivity of the zones 42 and 44, respectively. That is, the detectors $50_{E3G}$ and $50_{LH}$ measure the light passing through portions of the zones 42 and 44 not including the stripe areas. Photodetectors $54_{E3G}$ and $54_{LH}$ are employed to measure the light reduction properties of the E3G and LH stripe accumulations 46 and 47. Accordingly, the difference between the outputs of the light detectors $50_{E3G}$ and $54_{E3G}$ (as measured by a difference amplifier $60_{E3G}$) provides an analog measure of the amount of E3G metabolite in the urine. Similarly, a difference amplifier $60_{LH}$ provides an analog measure of urine LH by measuring the difference in outputs in the background and active area photodetectors $50_{LH}$ and $54_{LH}$.

The analog E3G value is converted to digital form in an analog-to-digital converter $65_{E3G}$ and the analog LH value is converted to digital form in an analog-to-digital converter $65_{LH}$. When activated via address bus 13 under control of the central processing unit 10, the digitized E3G and LH analyte measurements successively pass via a multiplexer 72 to addresses in the memory 18 via the data bus 15. The availability of measurement data is signalled by an activated "READ" switch 41. Switch 41 may be manually activated. Alternatively, the switch closure may occur automatically as via mechanical switch arm displacement upon test strip 40 insertion.

In summary then, the module 38 when activated by a user during an early morning urine measurement causes a digital value characterizing that day's measure value of E3G and that day's measure value of LH to be stored in memory 18. The data processing equipment of FIG. 1 then operates under stored program control to process that information, together with like information obtained and stored over a number of menstrual cycles to selectively activate the appropriate one of the "fertile" or "nonfertile" signalling light emitting diodes 86 or 88. Alternatively, the LH and E3G measurements may be made off-line, and entered into the composite FIG. 1 apparatus as by keyboard.

Figure 3A:
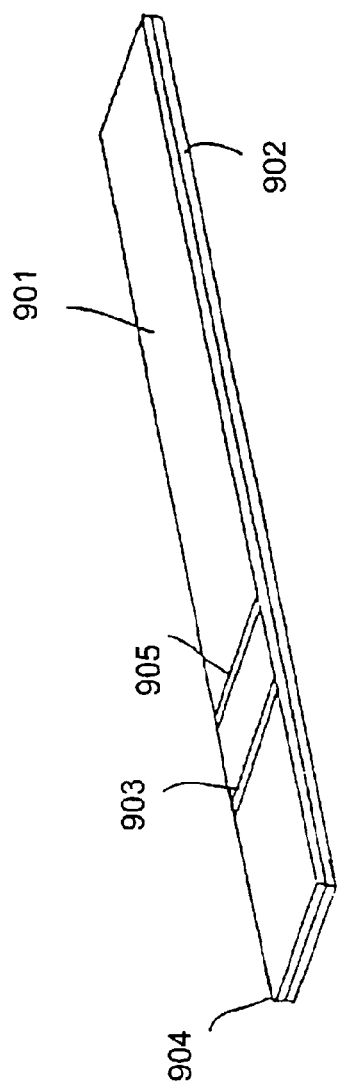
FIG. 3A depicts a dual-analyte test strip employed in the FIG. 1 apparatus.
Figure 3B:
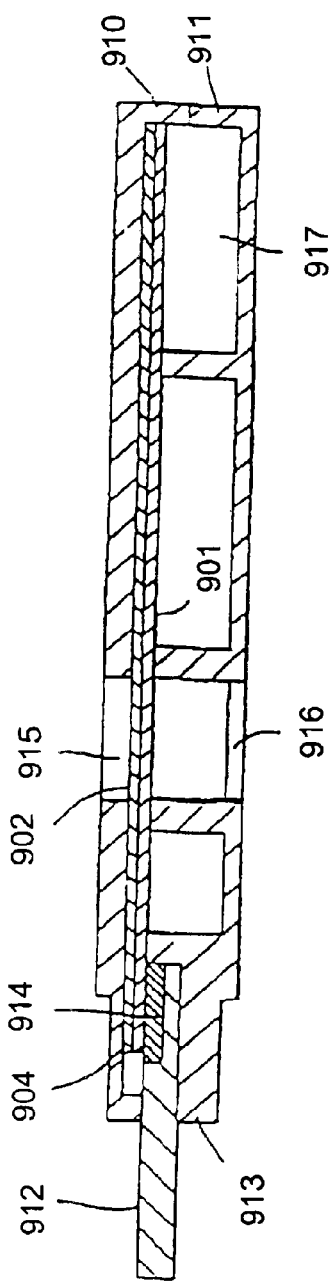
FIG. 3B depicts the assay test strip of FIG. 3A in longitudinal cross section.

A combined LH/E3G assay according to the invention is shown in FIGS. 3A and 3B. The physical construction and methods of manufacture of appropriate devices, including manufacture of reagents, are described in detail in EP-A-291194 and EP-A-383619, the disclosure of which are incorporated herein in their entirety.

The E3G latex (selective light occluding marker) is prepared by combining blue-colored latex particles (mean diameter 380 nm) with an anti-E3G monoclonal antibody of affinity in solution of about $10^{10}$ liters/mole. The antibody (170 μg/ml) is mixed with latex particles (0.5% solids) in a sodium borate buffer at pH 8.5. Vacant binding sites on the latex surface are blocked with BSA [25 mg/ml]. The latex is then washed to remove non-adsorbed materials.

The LH latex is prepared from an anti-beta LH monoclonal antibody adsorbed onto blue-colored latex particles (380 nm). This process is carried out with an antibody to latex ratio of 100 μg/ml to 0.5% solids in a sodium borate buffer (pH 8.5) containing ethanol (ratio of 6 to 1 v/v), followed by blocking the vacant binding sites with BSA (25 mg/ml). The latex is then washed to remove non-adsorbed materials.

A sheet (1.4 mm thick) of commercially-available, detergent pre-treated, macroporous polyethylene having a pore size of about 100 microns is saturated with an aqueous suspension of equal amounts of both populations of the latex particles as prepared above, 0.008% total solids, in a Tris buffer at pH 8.5 containing 3% BSA and 1% sugar. The sheet is freeze-dried and cut into portions each 6×12 mm, having a liquid capacity of about 50 μL.

The solid phase strip on which the levels of E3G and LH are detected is nitrocellulose, of 8μ nominal pore size, bonded to a polyester backing sheet. An E3G-protein (ovalbumen) conjugate, and an anti-alpha LH antibody, are separately plotted as lines onto the nitrocellulose at different locations (see FIGS. 3A–B) using solutions containing 2 mg/ml of the respective reagent in phosphate buffer at pH 7.4. The nitrocellulose is blocked with PVA before being cut into strips.

The above reagents are used in the assembly of an assay device as generally described and illustrated under embodiment 1 of EP-A-383619, the disclosure of which is incorporated by reference in its entirety.

FIGS. 3A and 3B of the accompanying drawings illustrate the device.

FIG. 3A shows the strip 901 of nitrocellulose on a backing strip 902 of transparent polyester. The strip has a length of 40 mm and width 6 mm. Line 903 (zone 44 in FIG. 1) represents the position of the anti-LH antibody immobilized on the strip. This line is approximately 1 mm wide and is centered 10 mm from the left hand end 904 of strip 1. Line 905 (zone 42 in FIG. 1) represents the position of the immobilized E3G. This is also a line of about 1 mm width and is centered 16 mm from the left hand end of the strip.

FIGS. 3A–3B show the assembled device in cross-section. The device comprises a casing having an upper half 910 and a lower half 911. A bibulous sample receiving member (wick) 912 protrudes from the left hand end 913 of the casing. The macroporous body 914 containing the two populations of latex particles is in contact with the wick within the casing. The casing also contains the strip 901 and its associated backing sheet 902. Sample liquid applied to the sample collector 912 can migrate via macroporous body 914 into strip 901. The casing has an upper aperture or window 914 and a lower aperture or window 916 arranged opposite one another such that light can be passed through the casing from one side to the other and in so doing will pass through a portion of the strip. This portion contains both reagent lines 903 and 905. Terminal portion 917 of the casing can contain a sink or desiccant, if desired.

When a urine sample containing LH and E3G is applied to the device it migrates via body 914 and into the strip. The two populations of latex particles are released and conveyed with the sample. Depending on the concentrations of the two analytes in the sample, the latex particles carrying the appropriate binding material become attached to the strip in the lines 903 and 905. The degree of binding of the particles in these lines can be determined by light transmission through the strip, as described in detail above.

The relative positioning of the E3G and LH lines, as described above, considerably enhances the efficiency with which the respective concentrations of the two analytes can be determined.

Figure 2:
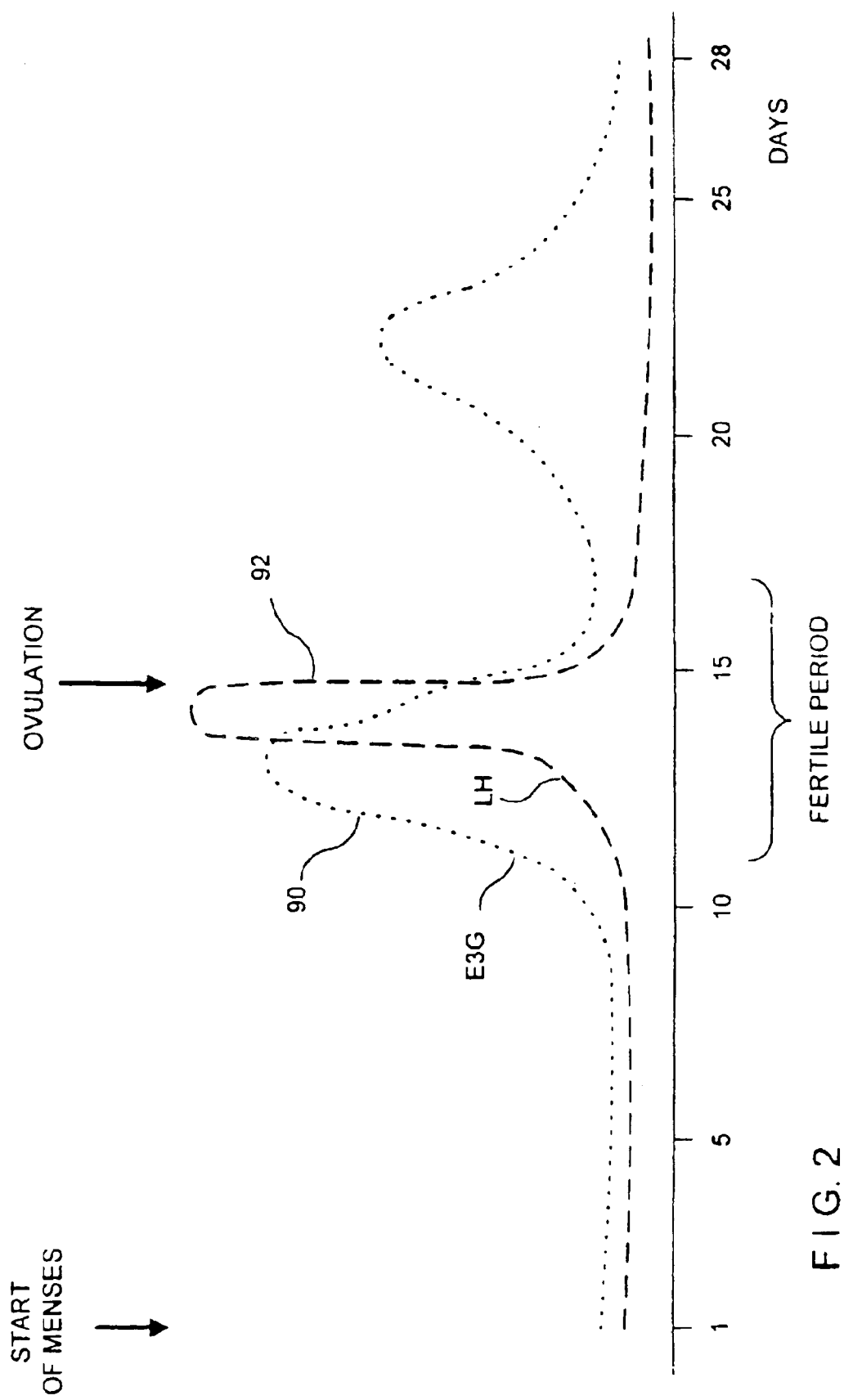
FIG. 2 is a diagram depicting the level of estrone-3-glucuronide ("E3G") and luteinizing hormone ("LH") over a typical monthly cycle.

Typical analyte levels for a particular subject are shown in FIG. 2 and have been generally discussed above. The E3G metabolite indicator of estradiol (dotted curve 90 in FIG. 2) begins at a low level, e.g., 11 ng/ml, at the beginning of the menstrual cycle. It begins to increase, more than doubling about 4 or 5 days before ovulation, and rises to a peak almost an order of magnitude larger than its early cycle level. E3G then falls off rapidly, increasing again late in the menstrual cycle. Similarly, the LH hormone also begins with a relatively low level of about 0 mIU/ml. It has a pronounced surge a day or so before ovulation, and then falls off rapidly. This is indicated by the dashed curve 92 in FIG. 2.

The inception of the fertile period will occur at a time when the E3G level increases significantly, representing the beginning of a period when sperm can survive and penetrate a changing, increasingly more sperm-hospitable form of cervical mucus. Fertility will end shortly after ovulation, i.e., several days after the LH surge (or after the E3G peak in the absence of an LH surge) beyond which time the female egg will no longer be viable. The various levels of the urine analytes over time thus serve as determinants for the inception and end of fertility in accordance with the algorithm discussed below.

The apparatus described above is operable in accordance with the program stored in memory 18. The algorithm which characterizes the program is set forth in flow chart form in FIGS. 4, 5 and 6. The program coding may be implemented in any program language per se well known to those skilled in the art. Illustrative instructions and instruction sequences will be shown in the BASIC language although, to repeat, any language will suffice. In the operation of the program the following variables are used:

OUTPUT VARIABLES

FRTL = Fertile period signal
NTFRTL = Notfertile period signal

INPUT & PROCESSING VARIABLES

TØDAY = the specific day within a menstrual cycle.
E3G(I, J) = the early morning estrone-3-glucuronide (E3G) signal level for the i-th day of the j-th month.
LH(I, J) = early morning urine luteinizing hormone (LH) level for the i-th day of the j-th month.
CMØ = cumulative mean day over the past menstrual cycles for the LH surge.
PKDAY(J) = measured LH surge day during the j-th measured menstrual cycle.
NØMØ = number of measurement days in the current menstrual cycle to date.
LHGTH = absolute LH threshold above which an LH surge is declared.
LHM = mean luteinizing hormone (LH) value during a particular monthly cycle.
THLD = relative LH indicating threshold, i.e., threshold relative to early cycle values.
BLØCK = Set to "0" until the LH surge (or E3G peak) is reached after which it changes to a "1" state.
LHPK = processing variable indicating whether the LH peak has occurred during the month.
E3GPK(J) = day corresponding to the peak value of E3G for the j-th cycle.

Figure 4:
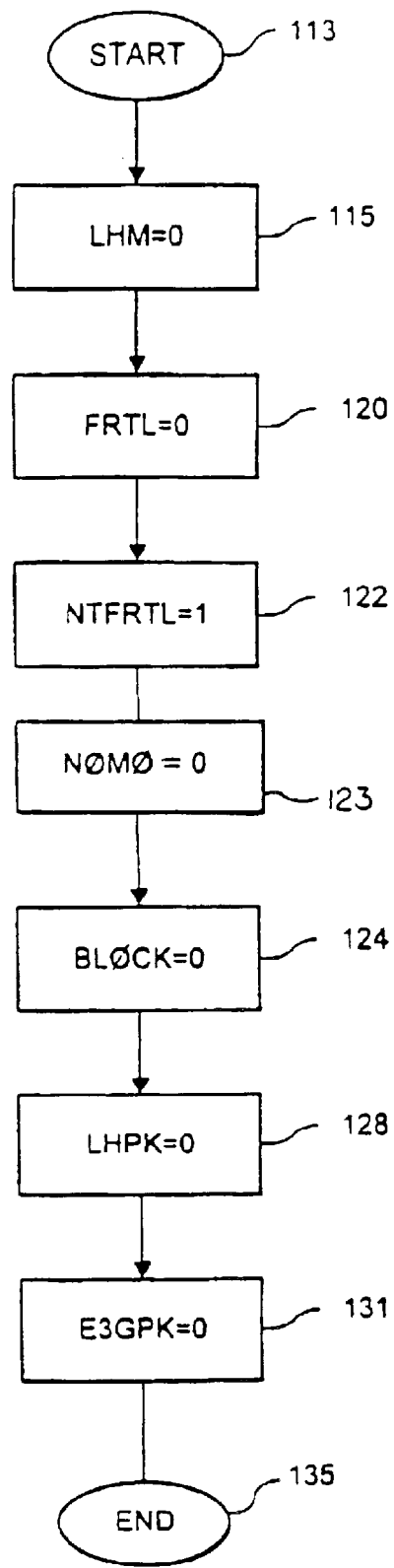
FIG. 4 is a flow chart for data processing characterizing the FIG. 1 apparatus at the beginning of a monthly cycle.

A specific illustrative system in which fertility is determined and signalled over the course of a typical menstrual cycle, i.e., a cycle after a specific female user has supplied LH and E3G data for several months will now be described. The system is initialized when the woman activates switch 39 the morning following menstruation. This resets a time base oscillator and clock 21 to day 1. The activated switch 39 signals the beginning of the month via interrupt port 11 of the central processing unit 10 which initializes the time base oscillator via the address and data buses 13 and 15. The CPU then performs its once per month initialization routine as represented by the flow chart of FIG. 4 emanating from a start node 113. Turning to FIG. 4, as a first matter, the mean luteinizing hormone (LH) level monthly parameter LHM is initialized to zero (step 115). Since the woman is nonfertile at this time, the fertility variable FRTL and the nonfertility variable NTFRTL are set to "0" and "1" respectively (steps 120 and 122). This loads the corresponding two cells $80_1$ and $80_2$ of latch 80 with a binary "0" and "1" to respectively illuminate the "nonfertility" signalling LED 88 and inactivate the "fertility" indicating LED 86 as discussed above. A variable NØMØ is made "0" (step 123) since no readings of E3G and/or LH have yet been taken for the new monitored monthly cycle.

A computational control variable BLØCK is initializied to "0" at step 124 to indicate that the ovulation precursor LH surge (or in its absence an E3G peak) has not yet occurred during the menstrual cycle. Similarly for initializing purposes, the computational variables LHPK and E3GPK are set to "0". These are control variables signalling that the respective LH and E3G readings have not yet reached their monthly peak values. That completes the apparatus monthly initialization of FIG. 4.

The FIG. 1 apparatus illuminates the "measure" (i.e., "take a measurement today") LED 87 by placing a "1" in the latch bit $80_3$ each morning when a measurement is to be taken. The first measurement is taken on day 6 of the month—a time which safely precedes any significant possibility of conception—computed as by "IF TODAY=6". When the memory lamp 89 is illuminated indicating to the user that a measurement is to be taken that day, she exposes a test strip 40 in her early morning urine and places the strip in the analyte measuring module 38 to produce E3G and LH measurements E3G(6,J) and LH(6,J). As indicated from the variable table above, the E3G and LH measurements are doubly subscripted variables. Thus, for example, the storage cell E3G(I,J) in memory 18 stores the digitized value of the E3G metabolite as measured the morning of the 6th day for the j-th measuring cycle. For present purposes, E3G(6,J) and LH(6,J) are the analyte values the 6th morning of the current (j-th) cycle. Since the computer maintains a running variable TØDAY, the variables could as well be written E3G (TØDAY,J) and LH(TØDAY,J). The variables for several preceding monthly cycles are also maintained in memory, the corresponding values for the preceding month being stored at memory 18 locations E3G(6,J-1) and LH(6,J-1).

Figure 5:
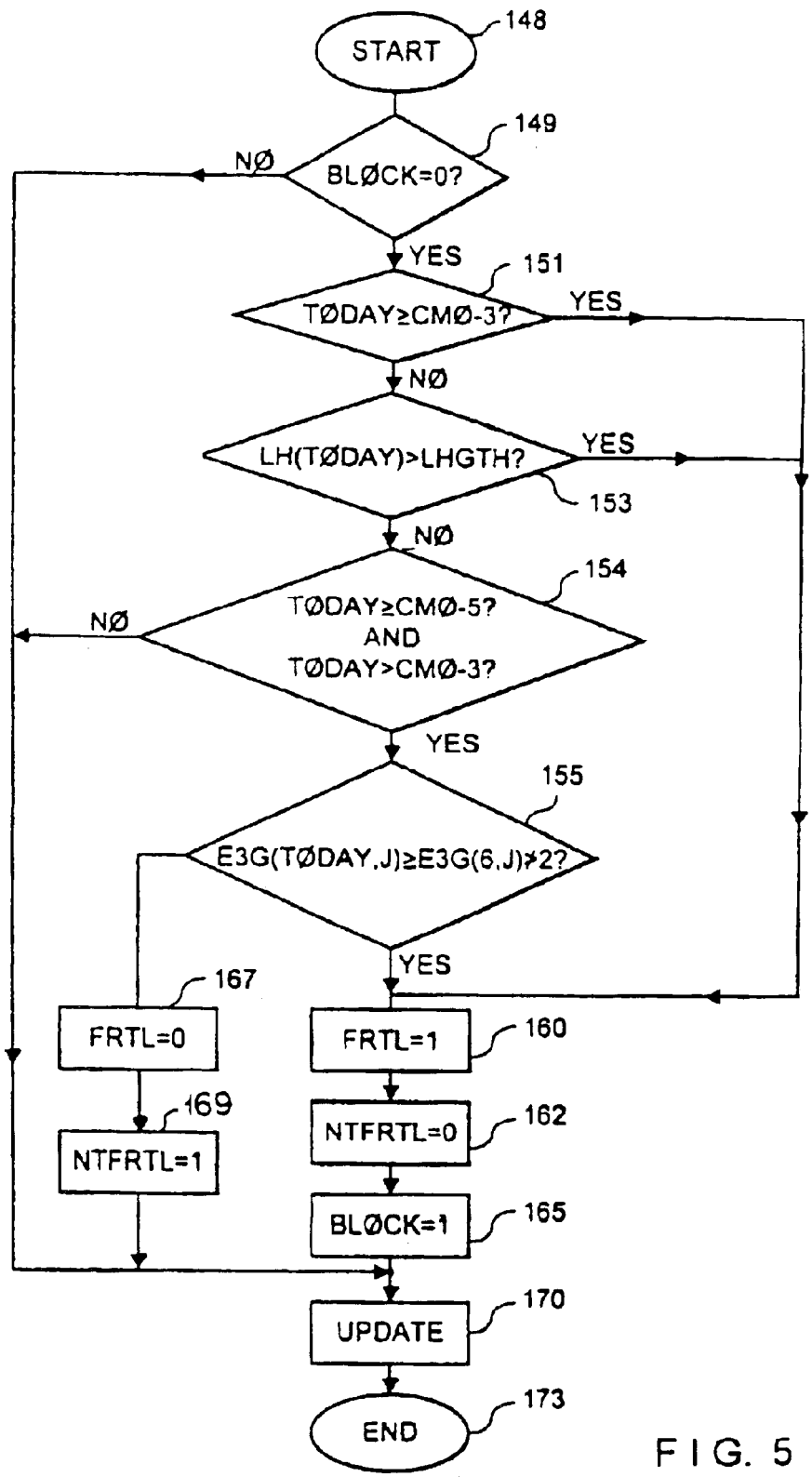
FIG. 5 is a flow chart for data processing characterizing the FIG. 1 apparatus when it recognizes and signals the beginning of a fertility period.

With the foregoing in mind, attention will now be directed to FIG. 5 which shows the processing each day to determine if a point of reasonably likely fertility has been attained. The processing begins at an entry node 148, first encountering a test 149 to determine whether the control variable BLØCK equals "0". If it does not, i.e., if BLØCK equals "1", that means that the beginning of fertility has already been achieved on an earlier day in the cycle and a NØ path from test 149 exits the routine to an END node 173 via a variable update step 170.

The step 170 updates the running cycle variables. For the day 6 test, the mean LH value LHM is revised to take into account LH(6,J). In general (since LHM is revised for all successive readings) the computation can result from:

K=1 TO NØMØ
LHM=LHM+LH(K,J)
NEXT K.
(recomputed average), or by $$LHM=(LHM*(NØMØ-1)+LH(TØDAY,J))/NØMØ$$

(updated unweighted average).

Assuming beginning of fertility had not yet been encountered for the cycle (YES result from the test 149, i.e., BLØCK equals "0"), a succeeding test 151 determines whether TØDAY (i.e., the number of today's day within the monthly cycle) is no earlier than 3 days prior to CMØ. CMØ is the average over the past six monthly cycles of the day when the woman's LH surge occurred. CMØ may be computed by:

FOR L=J-7 TO J-1
CMØ=CMØ+CMØ(L)
NEXT L.

Where L is any index variable.

When TØDAY is more than 3 days earlier than the projected surge day CMØ, a NØ branch from test 151 passes control to test 153. A YES result from test 151 (combined with BLØCK="0") means that the woman is within 3 days of her expected LH surge day without having earlier been found to be fertile. This is a sufficient condition to project possible fertility and, accordingly, the YES branch from test 151 proceeds to steps 160, 162 and 165. These respectively illuminate the "fertile" signalling LED 86 (FRTL=1), turn off the "nonfertile" LED 88 (NTFRTL=0), and set BLØCK to 1. That completes processing (END node 173) after variable updating (step 170).

Turning now to the NØ, more normal result of test 151, the following test 153 determines whether the LH hormone measured today (LH(TØDAY)) exceeds a stored absolute LH surge threshold value LHGTH. If it does not (the more usual result for BLØCK="0" data processing), program control passes to a test 154. However, should the absolute threshold LHGTH be exceeded, processing again passes to steps 160, 162 and 165 discussed above to signal a fertile condition and to set the control variable BLØCK to "1".

Test 154 examines the variable TØDAY and passes control to a test 155 if the value of the day within the menstrual cycle (TØDAY) is between five and three days prior to the expected ovulation precursor LH surge date CMØ. If it is not (NØ result), control passes to a step 170 to update computational variables and the routine ends. If TØDAY is the 5th or the 4th day before the woman's expected LH surge date (CMØ), that day's E3G reading E3G(TØDAY,J) is compared to the value of the E3G metabolite measured on day 6 of the cycle (E3G(6,J)). If today's value is at least twice the day 6 value, i.e., IF E3G(TØDAY,J)≧E3G(6,J)*2, that signals a significant increase in estradiol with its concomitant change in cervical mucus and sperm viability. Accordingly, the woman is declared to be in a fertile phase (YES output of test 157). This once again sets the light controls FRTL and INFRTL to an active and passive state, also setting BLØCK to "1" to indicate that the onset of fertility has been recognized at which point the processing ends for that day. Measurements are taken on day 6, and on day CMØ-5 and each of the eight days following CMØ-5.

In summary then, the processing of FIG. 5 recurs each day. It begins just after menstruation with FRTL=0 and NTFRTL=1, initially having an output "nonfertile" active display. This changes, as appropriate during the monthly cycle, when a pronounced increase in the E3G metabolite is encountered; when an LH surge is sensed; or if sufficient time passes so that the woman is within three days of her expected LH surge.

The foregoing FIG. 4 processing describes system operation which declares and maintains the onset of a "fertile" phase output following a post-menstruation "nonfertile" indication period.

Figure 6:
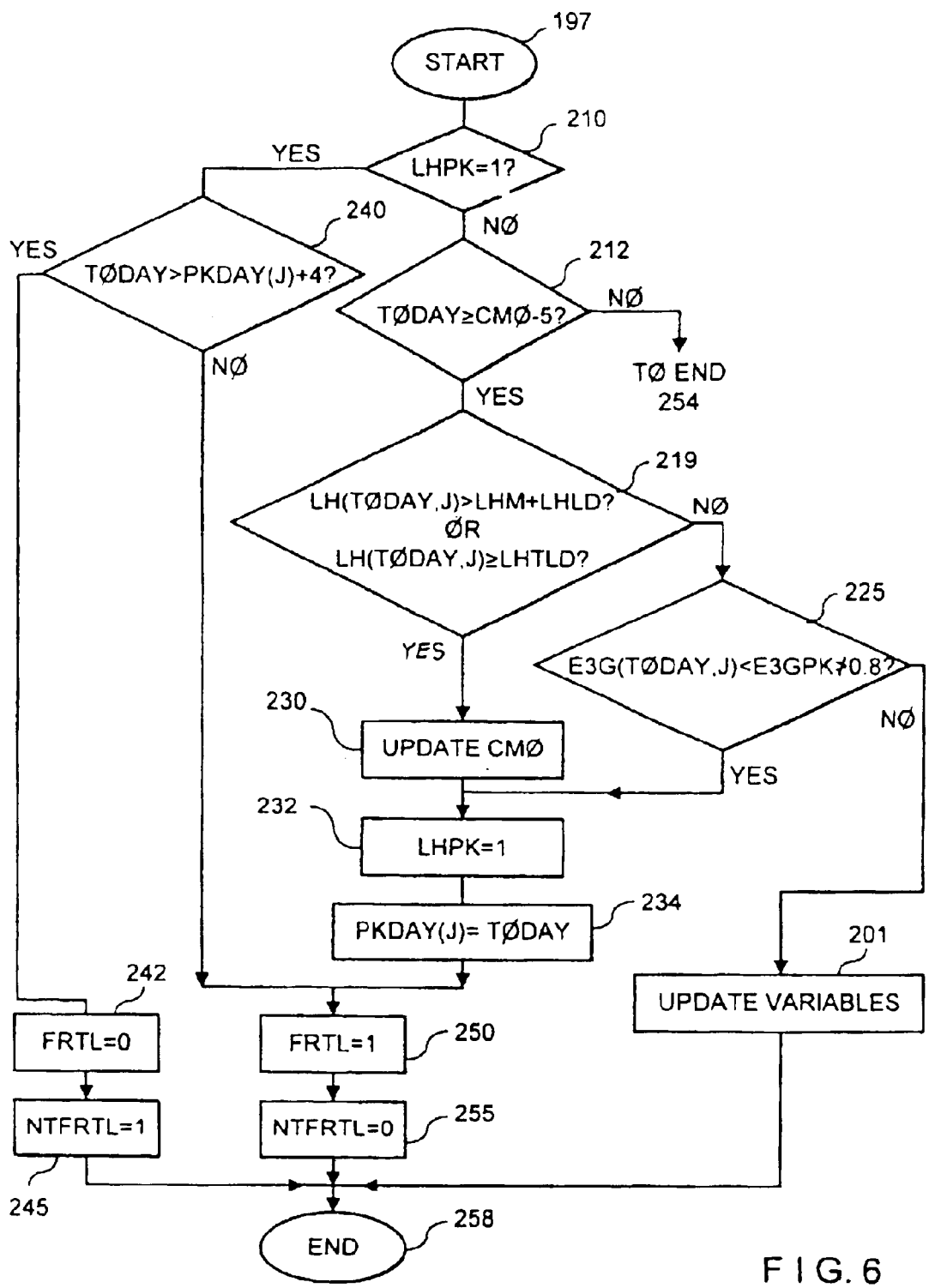
FIG. 6 is a flow chart for data processing characterizing the FIG. 1 apparatus as it determines and signals the end of the fertile period.

Referring now to FIG. 6, there is shown a flow chart for system processing which ends the "fertile" period for the remainder of the menstrual cycle. Data processing passes from a start or entry node 197 to a first test 210 of a computational control variable LHPK (representing that the LH surge has/has not occurred). The variable LHPK was initialized to "0" at the beginning of the monthly cycle (step 128 of FIG. 4) to indicate that the LH surge had not yet occurred. Assuming this to be the case (NØ output of test 210), control passes to test 212. Test 212 determines whether or not a point in the cycle had been reached (value of TØDAY) which is no earlier than five days before the expected LH surge. If such a date has not yet been achieved (NØ test output), control passes to a routine end node 258. This leaves the previous fertility output state (for mid-month processing) intact.

Assuming that the LH surge had not been achieved (NØ branch from test 210 meaning that LHPK="0") and that the data processing day is at least CMØ-5 (YES branch from test 112), system control passes to test 219. Test 219 compares the value measured day for the luteinizing hormone (LH (TØDAY,J)) with the sum of the average value for LH measured over the current cycle (LHM) plus a relative threshold amount THLD. If the value LH(TØDAY,J) does not exceed the average value plus the surge threshold (THLD), the LH surge does not yet exist (NØ) (unless LH(TØDAY,J) is greater than the absolution threshold LHTCD). Following this NØ branch of test 219, test 225 determines whether a peak has occurred for the E3G metabolite, as by the test:

IF E3G(I,J)<E3GPK*0.8.

If the test is not satisfied, i.e., if a peak in E3G has not been achieved (the E3G value today is less than 80% of the peak value measured for the cycle E3GPK), NØ branch processing results from test 225. This NØ branch means that neither the LH surge peak (test 219) nor the E3G peak (test 225) has occurred. Accordingly, neither of the precursor conditions for ovulation had yet happened. NØ branch processing from the tests 219 and 225 updates the LHM monthly variable and updates the E3G peak value (step 201) and processing on point ends (node 254) for that day's processing. The intra-month LH median variable LHM updating occurs in a manner directly analogous to that for the variable LHM discussed above.

However, when the LH surge is recognized (YES output of test 219), the LH peak or flag bit variable LHPK is set to "1" (step 232) to signal this fact. Either before or after this occurs, the variable CMØ is updated by recomputing the most recent six month average period until recognition of LH surge (step 230). This is used in the next month's processing. Finally, the day of occurrence of the LH surge peak for the current month (PKDAY(J)) is stored (step 234).

After such peak day recognition occurs, processing reaches the end node 258 via operations 250 and 255 which maintain output signalling in the "fertile" mode with FRTL= "1" and NTFRTL="0". Fertility is maintained since sperm and egg survivability extends beyond the LH surge (or E3G peak) until a day or two past ovulation which, in turn, comes shortly after the LH surge. It will be observed that a YES response from test 225 (signalling the fact that the E3G metabolite has passed its peak value later than five days before the expected LH surge (YES response of test 212)) but in the absence of an LH surge (NØ path from test 219) similarly acts to set the LHPK flag bit and store a peak value day.

For data processing on days later than the LH surge (or post-E3G peak), the flag bit LHPK has been set to "1" and thus all further processing follows the YES branch of test 210. Test 240 determines whether the processing day is at least four days past the peak day. If it is not (NØ branch), the fertile condition and output signalling remains via operations 250 and 255. At times at least four days after the peak LH surge or E3G metabolite peak was determined (YES branch of test 240), data processing passes to steps 242 and 245 to respectively deactivate the fertile LED 86 by setting FRTL="0", and illuminate the "nonfertile" signalling LED 88.

Accordingly, the data processing described above provides an output indication throughout an ovulation cycle of the fertility state of the subject by selectively controlling the active/inactive state of the "fertile" and "nonfertile" LEDs 86 and 88.

The foregoing discussion has been for typical, ongoing periods of time after data has been collected for the subject for a sufficient number of cycles to characterize the physical persona of a specific individual user with some confidence. There are several methodologies which may be employed for initial, early months (as set forth in said application Ser. No. 532,457). These include using data gathered from studies over a substantial female population, employing significant safety margins to expand the "fertile" output signalling duration. Alternatively, the inception of fertility can result from processing analogous to that shown in FIG. 5 (using population data for the equivalent of CMØ rather than past history of the subject), with a date override of conservative bound such that fertility is signalled at some point earlier than CMØ-3. Similarly, end of fertility may be indicated by processing analogous to that of FIG. 5, subject to a date override substantially longer than CMØ+4.

The above described system and methodology is merely illustrative of the principles of the present invention. Numerous modifications and adaptations thereof may be readily apparent to those skilled in the art without departing from the spirit and scope of the present invention.

What is claimed is:

1. A method for determining the fertility state of a female during her menstrual cycle comprising the steps of measuring estrone-3-glucuronide ("E3G") and luteinizing hormone ("LH") early in the cycle, predicting the date of LH surge for the cycle, measuring E3G and LH in urine on predetermined days in advance of and continuing at least to the projected LH surge date, providing a fertile output indication when the measured E3G level significantly exceeds the early cycle E3G value, and providing a nonfertile indication a period of time after the measured LH hormone value exceeds its early cycle amounts.

2. A method as in claim 1 wherein said LH surge, predicting step employs a statistic dependent upon the day-within-cycle of the LH surge for a plurality of earlier cycles.

3. A method for determining the end of fertility state of a female during her menstrual cycle comprising the steps of measuring luteinizing hormone ("LH") early in the cycle, predicting the date of LH surge for the cycle, and measuring LH in urine on predetermined days in advance of and continuing at least to the projected LH surge date, and providing a nonfertile indication a period of time after the measured LH hormone value exceeds its early cycle amounts.

4. A method as in claim 3 wherein said LH surge, predicting step employs a statistic dependent upon the day-within-cycle of the LH surge for a plurality of earlier cycles.

* * * * *